(12) United States Patent
Mohapatra et al.

(10) Patent No.: US 9,091,640 B1
(45) Date of Patent: Jul. 28, 2015

(54) CHITOSAN-GRAPHENE BIOSENSORS AND METHODS FOR THEIR USE

(71) Applicants: Shyam S. Mohapatra, Lutz, FL (US); Kyle A. Cissell, Saginaw, MI (US); Subbiah Alwarappan, Tampa, FL (US)

(72) Inventors: Shyam S. Mohapatra, Lutz, FL (US); Kyle A. Cissell, Saginaw, MI (US); Subbiah Alwarappan, Tampa, FL (US)

(73) Assignees: University of South Florida, Tampa, FL (US); TransGenex Therapeutics, LLC, Tampa, FL (US)

( * ) Notice: Subject to any disclaimer, the term of this patent is extended or adjusted under 35 U.S.C. 154(b) by 0 days.

(21) Appl. No.: 14/028,920

(22) Filed: Sep. 17, 2013

Related U.S. Application Data (60) Provisional application No. 61/701,754, filed on Sep. 17, 2012.

(51) Int. Cl.
*G01N 27/30* (2006.01)

(52) U.S. Cl.
CPC .................................. *G01N 27/307* (2013.01)

(58) Field of Classification Search
CPC .......... G01N 27/3275–27/3278; G01N 27/307
USPC ........ 204/403.01, 228.6, 228.9, 229.4–229.7, 204/280, 294; 977/738, 778, 779, 784, 788, 977/795, 796, 892, 920
See application file for complete search history.

(56) References Cited

U.S. PATENT DOCUMENTS

2010/0116691 A1   5/2010   Papadimitrakopoulos et al.

OTHER PUBLICATIONS

Y. Yang, et al. "Electrical detection of deoxyribonucleic acid hybridization based on carbon-nanotubes/nano zirconium dioxide/chitosan-modified electrode" Analytica Chimica Acta, vol. 584, 2007, p. 268-274.*
Neto, AH Castro, et al. "The electronic properties of graphene." Reviews of modern physics 81.1 (2009): 109.
Peres, N. M. R., F. Guinea, and AH Castro Neto. "Electronic properties of disordered two-dimensional carbon." Physical Review B 73.12 (2006): 125411.
Novoselov, K. S., et al. "Electronic properties of graphene." physica status solidi (b) 244.11 (2007): 4106-4111.
Booth, Tim J., et al. "Macroscopic graphene membranes and their extraordinary stiffness." Nano letters 8.8 (2008): 2442-2446.
Meyer, J. C., et al. "On the roughness of single-and bi-layer graphene membranes." Solid State Communications 143.1 (2007): 101-109.
Scharfenberg, Scott, et al. "Probing the mechanical properties of graphene using a corrugated elastic substrate." Applied Physics Letters 98.9 (2011): 091908-091908.
Balandin, Alexander A. "Thermal properties of graphene and nanostructured carbon materials." Nature materials 10.8 (2011): 569-581.
Balandin, Alexander A., et al. "Superior thermal conductivity of single-layer graphene." Nano letters 8.3 (2008): 902-907.

(Continued)

*Primary Examiner* — J. Christopher Ball
(74) *Attorney, Agent, or Firm* — Thomas | Horstemeyer, LLP (57) ABSTRACT

Provided herein is a method for detecting mutations in polynucleotide sequences through the use of a glassy carbon electrode (GCE) coated with a chitosan-graphene nanosheet material (also referred to herein as a "CMG electrode.") It is a surprising finding of the present invention that the CMG electrodes can be used to detect non-hybridization of capture and target polynucleotides using voltammetry, wherein non-hybridization indicates a mutation or difference in the target polynucleotide as compared to a control.

10 Claims, 4 Drawing Sheets

(56) References Cited

OTHER PUBLICATIONS

Kim, Keun Soo, et al. "Large-scale pattern growth of graphene films for stretchable transparent electrodes." Nature 457.7230 (2009): 706-710.

Han, Melinda Y., Juliana C. Brant, and Philip Kim. "Electron transport in disordered graphene nanoribbons." Physical review letters 104.5 (2010): 056801.

Tang, Zhiwen, et al. "Constraint of DNA on functionalized graphene improves its biostability and specificity." Small 6.11 (2010): 1205-1209.

Seger, Brian, and Prashant V. Kamat. "Electrocatalytically active graphene-platinum nanocomposites. Role of 2-D carbon support in PEM fuel cells." The Journal of Physical Chemistry C 113.19 (2009): 7990-7995.

Stoller, Meryl D., et al. "Graphene-based ultracapacitors." Nano letters 8.10 (2008): 3498-3502.

Bunch, J. Scott, et al. "Electromechanical resonators from graphene sheets." Science 315.5811 (2007): 490-493.

Lin, Yu-Ming, et al. "Operation of graphene transistors at gigahertz frequencies." Nano Letters 9.1 (2008): 422-426.

Tuinstra, F., and J. L. Koenig. "Raman spectrum of graphite." The Journal of Chemical Physics 53 (1970): 1126.

Ferrari, A. C., et al. "Raman spectrum of graphene and graphene layers." Physical review letters 97.18 (2006): 187401.

Ferrari, A. C., and J. Robertson. "Interpretation of Raman spectra of disordered and amorphous carbon." Physical review B 61.20 (2000): 14095.

Piscanec, S., et al. "Kohn anomalies and electron-phonon interactions in graphite." Physical review letters 93.18 (2004): 185503.

Wang, et al. "A glucose biosensor based on Prussian blue/chitosan hybrid film." Biosensors and Bioelectronics 24 (2009) 1527-1530.

Sun, et al. "Application of chitosan/Fe3O4 microsphere—graphene composite modified carbon ionic liquid electrode for the electrochemical detection of the PCR product of soybean Lectin gene sequence." SciVerse ScienceDirect (2011) 106-112.

Kang, et al. "Glucose Oxidase—graphene—chitosan modified electrode for direct electrochemistry and glucose sensing." ScienceDirect, Biosensors and Bioelectronics 25 (2009) 901-905.

Zhou, et al. "Electrochemical Sensing and Biosensing Platform Based on Chemically Reduced Graphene Oxide." Anal. Chem. 2009, 81, 5603-5613.

Qi, et al. "Electrochemical DNA biosensor with chitosan-Co3O4 nanorod-graphene composite for the sensitive detection of *Staphylococcus aureus* nuc gene sequence." SciVerse ScienceDirect, Bioelectrochemistry 88 (2012) 42-77.

\* cited by examiner

CHITOSAN-GRAPHENE BIOSENSORS AND METHODS FOR THEIR USE

CROSS REFERENCE TO RELATED APPLICATIONS

This application claims the priority benefit of U.S. Provisional Patent Application Ser. No. 61/701,754 filed Sep. 17, 2012.

BACKGROUND OF THE INVENTION

1) Field of the Invention

The present invention relates to the field of graphene biosensors.

2) Description of Related Art

Graphene [Novoselov, K. S. et al. Science 306.5696 (2004)], one of the exotic new nanomaterials of the 21st century, is a two-dimensional sheet comprised solely of sp2 carbon atoms arranged in a chicken-wire like framework [Geim, A. K. & P. Kim. Scientific American 298.4 (2008); Geim, A. K. Science 324.5934 (2009); V. I. Falko, A. K. Geim, Eur. Phy. J—Special Topics 148 (2007); Schedin, F. et al. Nature materials 6.9 (2007)]. Graphene possesses outstanding electronic [Neto, A. H. C. et al. Reviews of modern physics 81.1 (2009); Peres, N. M. R., F. Guinea, & A. H. C. Neto. Physical Review B 73.12 (2006); Novoselov, K. S. et al. Physica status solidi (B) 244.11 (2007)], mechanical [Booth, T. J. et al. Nano letters 8.8 (2008); Meyer, J. C. et al. Solid State Communications 143.1 (2007); Scharfenberg, Scott, et al. Applied Physics Letters 98.9 (2011)], thermal [Clement, F. et al. CS Nano 4 (2010); Balandin, Alexander A. Nature materials 10.8 (2011); Balandin, A. A. et al. Nano letters 8.3 (2008)], optical [Kim, K. S. et al. Nature 457.7230 (2009); Bae, S. et al. Nature nanotechnology 5.8 (2010)] and charge transport [Cho, S. & M. S. Fuhrer. Physical Review B 77.8 (2008); Han, M. Y. et al. Physical review letters 104.5 (2010)] properties that make it an attractive choice for biosensors [Alwarappan, S. et al. Journal of Physical Chemistry C 113.20 (2009); Alwarappan, S. et al. Journal of Physical Chemistry C 114.30 (2010); Tang, Z. et al. Small 6.11 (2010); L. Zhu et al. Biosens. and Bioelectron. 35 (2012); F. Li et al. Nanoscale 2.6 (2010)], fuel cells [Liu, C. et al. Biosensors and Bioelectronics 25.7 (2010); Seger, B. & P. Kamat. Journal of Physical Chemistry C 113.19 (2009)], batteries [Wu, Z.-S. et al. ACS nano 4.6 (2010); Min, P. S. et al. Nano letters, 9 (2009)], ultracapacitors [Stoller, M. D. et al. Nano letters 8.10 (2008); Liu, C. et al. Nano letters 10.12 (2010)], electromechanical resonators [Bunch, J. S. et al. Science 315.5811 (2007); Chen, C. et al. Nature nanotechnology 4.12 (2009)] and field effect transistors [Lin, Y.-M. et al. Nano Letters 9.1 (2008); Schwierz, F. Nature nanotechnology 5.7 (2010)].

Altered DNA sequences in specific genes are characteristic of many diseases from cancer to asthma and their identification is important for correct diagnosis and treatment. While DNA mutations or single-nucleotide polymorphisms can be detected by direct sequencing or PCR, these methods require costly instruments, extensive training and relatively long run times. A rapid, inexpensive, specific, and sensitive device for detecting mismatched DNAs that could be used in the field or during a clinic visit would prove invaluable to physicians, especially in resource-limited areas.

BRIEF DESCRIPTION OF THE DRAWINGS

FIG. 1 (A and B) shows a Raman spectrogram (A) and transmission electron micrograph (B) of graphene.

DETAILED DESCRIPTION OF THE INVENTION

Provided herein is a method for detecting mutations in polynucleotide sequences through the use of a glassy carbon electrode (GCE) coated with a chitosan-graphene nanosheet material (also referred to herein as a "CMG electrode.") It is a surprising finding of the present invention that the CMG electrodes can be used to detect non-hybridization of capture and target polynucleotides using voltammetry, wherein non-hybridization indicates a mutation or difference in the target polynucleotide as compared to a control. Term definitions used in the specification and claims are as follows.

DEFINITIONS

As used in the specification and claims, the singular form "a," "an," and "the" include plural references unless the context clearly dictates otherwise. For example, the term "a polynucleotide" includes a plurality of polynucleotides, including mixtures thereof.

The term "chitosan" refers to a linear polysaccharide composed of randomly distributed β-(1-4)-linked D-glucosamine (deacetylated unit) and N-acetyl-D-glucosamine (acetylated unit). The degree of deacetylation (% DD) can be determined by NMR spectroscopy, and the % DD in commercial chitosans ranges from 60 to 100%. On average, the molecular weight of commercially produced chitosan is between 3800 and 20,000 Daltons. In some embodiments, the chitosan has a molecular weight of 10,000 Daltons.

The term "chitosan-graphene nanosheet material" refers herein to a planar material comprising chitosan and graphene. Graphene is an allotrope of carbon whose structure is a single planar sheet of $sp^2$-bonded carbon atoms that are densely packed in a honeycomb crystal lattice. The carbon-carbon bond length in graphene is about 0.142 nanometers. Graphene sheets stack to form graphite with an interplanar spacing of approximately 0.335 nm. However, as used herein, the term "chitosan-graphene nanosheet" refers not only to a single planar sheet of $sp^2$-bonded carbon atoms and chitosan, but also refers to a composition comprising chitosan and multiple graphene sheets stacked upon one another. In one embodiment, the chitosan-graphene nanosheet material comprises approximately 7 sheets.

As used herein, the term "comprising" is intended to mean that the compositions and methods include the recited elements, but not excluding others. "Consisting essentially" of when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative." A "hybridizing control polynucleotide" refers to a polynucleotide that is complementary to the capture polynucleotide, such complementarity resulting in the hybridization of the control and capture polynucleotide under appropriate hybridization conditions. In some embodiments, the control polynucleotide is 100% complementary to the capture polynucleotide.

The term "cyclic voltammetry" refers herein to a type of potentiodynamic electrochemical measurement. In a cyclic voltammetry experiment, the working electrode potential is ramped linearly versus time. When cyclic voltammetry reaches a set potential, the working electrode's potential ramp is inverted. This inversion can happen multiple times during a single experiment. The current at the working electrode is plotted versus the applied voltage to give the cyclic voltammogram trace. The cyclic voltammetry method uses a reference electrode, working electrode, and counter electrode which in combination are sometimes referred to as a three-electrode setup. Electrolyte is usually added to the test solution to ensure sufficient conductivity. The combination of the solvent, electrolyte and specific working electrode material determines the range of the potential. Electrodes are static and sit in unstirred solutions during cyclic voltammetry. This "still" solution method results in cyclic voltammetry's characteristic diffusion controlled peaks.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, or any combination of these.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

The term "glassy carbon" refers herein to a non-graphitizing carbon which combines glassy and ceramic properties with those of graphite. The most important properties are high temperature resistance, hardness (7 Mohs), low density, low electrical resistance, low friction, low thermal resistance, extreme resistance to chemical attack, and impermeability to gases and liquids.

The terms "polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also refers to both double- and single-stranded molecules.

A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. Complementary bases are A and T, C and G, and A and U.

DESCRIPTION

This invention pertains to a chitosan-modified graphene platform for the electrochemical detection of changes in DNA sequences. For this purpose, graphene synthesized chemically and characterized by Raman spectroscopy and Transmission electron microscopy, was covalently modified with positively charged chitosan to facilitate the immobilization of a single-stranded DNA 'capture' oligonucleotide. The covalent attachment of chitosan to graphene was confirmed by FT-IR spectroscopy and then the capture DNA was immobilized on to the chitosan modified graphene electrode. Then, the target DNA (complementary or mismatched 'mutant' DNA) was applied to the electrode and cyclic voltammetry was performed. The results of the voltammetric experiments indicate that the chitosan modified graphene electrodes immobilized with ssDNA+complementary DNA exhibit a significantly higher magnitude of redox peak current than the chitosan modified graphene electrodes immobilized with the non-complementary mutant DNAs. Together, these results demonstrate that the chitosan-graphene platform provides a rapid, stable and sensitive detection of mismatched DNA and has the potential to be used for point-of-care diagnostic tests for specific DNA mutations associated with disease conditions.

Accordingly, provided herein is a method for detecting non-hybridization of polynucleotide sequences comprising 1) providing a glassy carbon electrode (GCE) coated with a chitosan-graphene nanosheet material and having a single stranded capture polynucleotide attached thereto; 2) adding a single stranded target polynucleotide to the GCE and allowing sufficient time for hybridization of the capture and target polynucleotides; 3) removing the unbound target polynucleotide; and 4) subjecting the GCE to cyclic voltammetry; wherein a decrease in a voltammetric peak as compared to a hybridizing control polynucleotide indicates non-hybridization of the capture and target polynucleotides. In some embodiments, non-hybridization indicates a mutation in the target polynucleotide as compared to the control polynucleotide.

It should be understood that "unbound" target polynucleotide will be that polynucleotide that either 1) does not hybridize to the capture polynucleotide or 2) does not bind non-specifically to the GCE. Non-complementary target polynucleotide does not hybridize to the capture polynucleotide but it does bind electrostatically to the surface of the CMG electrode itself in a non-specific manner. It is this non-specific binding to the CMG that causes a blockage of the ions diffusing towards the electrode surface during cyclic voltammetry, and thus causes a decrease in the voltammetric peak as compared to a hybridizing control. Accordingly, the present invention provides a means for testing for a non-homologous target polynucleotide as compared to a control polynucleotide.

A decrease in the voltammetric peak will be obtained when the target polynucleotide is less than 100% complementary to the capture polynucleotide (and less than 100% homologous to the control polynucleotide), and therefore, does not hybridize to the capture polynucleotide. Higher stringency conditions will be required in order to identify a target polynucleotide having a higher percentage homology less than 100% (or lower number of mutations) as compared to the control polynucleotide. Accordingly, the present invention includes a method of detecting a mutation in a target polynucleotide sequence comprising 1) providing a glassy carbon electrode (GCE) coated with a chitosan-graphene nanosheet material and having a single stranded capture polynucleotide attached thereto; 2) adding the single stranded target polynucleotide to the GCE and allowing sufficient time for binding of the capture and target polynucleotides; 3) removing the unbound target polynucleotide; and 4) subjecting the GCE to cyclic voltammetry; wherein a decrease in a voltammetric peak as compared to a hybridizing control indicates a mutation in the target polynucleotide as compared to the control.

In some embodiments, the target polynucleotide has approximately 60%, 70%, 80%, 90%, 95%, or 98% homology with a control polynucleotide that is approximately 100% complementary to a capture polynucleotide. The length of the target and capture polynucleotides, the G and C content of the polynucleotides, the hybridization temperature, and salt conditions will each affect hybridization. Where $T_m=69.3°$ C.$+0.41$ (% G+C)° C., a 1% mismatch between the hybridizing polynucleotides lowers the $T_m$ by 1.4° C. When taking into effect the salt concentration, the effective $T_m=81.5+16.6$ (log M[Na$^+$])+0.41 (% G+C)° C.$-0.72$ (% formamide). In some embodiments, the capture, target, and/or control polynucleotides are approximately 5, 8, 10, 15, 20, 25, 30, or 40 nucleotides in length.

The chitosan-graphene nanosheet material can comprise any amount of chitosan and graphene that results in planar sheets of sp$^2$-bonded carbon atoms that are densely packed in a honeycomb crystal lattice. In some embodiments, the chitosan-graphene nanosheet material comprises approximately five, six, seven, eight, or nine planar sheets. In one embodiment, the chitosan-graphene nanosheet material comprises approximately seven planar sheets. In other or further embodiments, the FT-IR spectrum of the chitosan-graphene nanosheet material exhibits IR peaks at approximately 2920 cm$^{-1}$ and 2849 cm$^{-1}$ (sp$^2$ $v_{C-H}$ stretching), approximately 1731 cm$^{-1}$ and 1626 cm$^{-1}$ ($v_{C=O}$), approximately 1481 cm$^{-1}$ (skeletal vibrations of graphene sheets), approximately 1461 cm$^{-1}$ (carboxyl $v_{C-O}$ stretching), approximately 1177 cm$^{-1}$ (alkoxy $v_{C-O}$ stretching at the edges of graphene), approximately 1051 cm$^{-1}$ ($v_{C-O}$ stretching), and approximately 1635 cm$^{-1}$ ($v_{CONH}$).

The ratio of chitosan to graphene in the nanosheet material can be approximately 1:2, 1:1, or 2:1. In some embodiments, the chitosan-graphene nanosheet material is prepared using an approximately 0.020%, 0.010%, 0.005%, or 0.002% (w/v) graphene solution. In other or further embodiments, the chitosan-graphene nanosheet material is prepared using an approximately 0.020%, 0.010%, 0.005%, or 0.002% (w/v) chitosan solution.

It is to be understood that the GCE coated with a chitosan-graphene nanosheet material having a single stranded capture polynucleotide attached thereto can be subjected to any form of cyclic voltammetry known to those of skill in the art. In some embodiments, the working, reference and counter electrode(s) are CMG, Ag/AgCl (3.0M KCl), and platinum wire, respectively. In other or further embodiments, the cyclic voltammetry is performed using $K_4[Fe(CN)_6]^{3-/4-}$ as the redox probe.

In addition to methods of detecting non-hybridization and/or mutation of a target polynucleotide as compared to a control polynucleotide, provided herein is a device for detecting non-hybridization of polynucleotide sequences and a method for making the device. The device comprises a glassy carbon electrode (GCE) coated with a chitosan-graphene nanosheet material. In some embodiments, the device further comprises a single stranded capture polynucleotide.

The GCE used in the device and method of making the device can be any GCE known to those of skill in the art. The term "glassy carbon" refers herein to a non-graphitizing carbon which combines glassy and ceramic properties with those of graphite. The most important properties are high temperature resistance, hardness (7 Mohs), low density, low electrical resistance, low friction, low thermal resistance, extreme resistance to chemical attack, and impermeability to gases and liquids.

The GCE is coated with a chitosan-graphene nanosheet material described herein. It should be understood that the terms "coated" and "coating" do not require complete coverage of the GCE with the chitosan-graphene nanosheet material. In some embodiments, a suspension of chitosan-graphene nanosheet material is pipetted onto the surface of a GCE.

The chitosan-graphene nanosheet material of the device can be any such material described above or below. In particular, the chitosan-graphene nanosheet material can comprise any amount of chitosan and graphene that results in planar sheets of sp$^2$-bonded carbon atoms that are densely packed in a honeycomb crystal lattice. In some embodiments, the chitosan-graphene nanosheet material comprises approximately five, six, seven, eight, or nine planar sheets. In one embodiment, the chitosan-graphene nanosheet material comprises approximately seven planar sheets. In other or further embodiments, the FT-IR spectrum analysis of the chitosan-graphene nanosheet material exhibits IR peaks at approximately 2920 cm$^{-1}$ and 2849 cm$^{-1}$ (sp$^2$ $v_{C-H}$ stretching), approximately 1731 cm$^{-1}$ and 1626 cm$^{-1}$ ($v_{C-O}$), approximately 1481 cm$^{-1}$ (skeletal vibrations of graphene sheets), approximately 1461 cm$^{-1}$ (carboxyl $v_{C-O}$ stretching), approximately 1177 cm$^{-1}$ (alkoxy $v_{C-O}$ stretching at the edges of graphene), approximately 1051 cm$^{-1}$ ($v_{C-O}$ stretching), and approximately 1635 cm$^{-1}$ ($v_{CONH}$).

The ratio of chitosan to graphene in the nanosheet material can be approximately 1:2, 1:1, or 2:1. In some embodiments, the chitosan-graphene nanosheet material is prepared using an approximately 0.020%, 0.010%, 0.005%, or 0.002% (w/v) graphene solution. In other or further embodiments, the chitosan-graphene nanosheet material is prepared using an approximately 0.020%, 0.010%, 0.005%, or 0.002% (w/v) chitosan solution.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

EXAMPLES

Example 1

Synthesis of Chitosan-Modified Graphene

Graphene was synthesized according to the method described in Alwarappan, S. et al. [Journal of Physical Chemistry C 113.20 (2009)]. Graphene oxide (GO) was synthesized by following Hummers method [Hummers Jr., W. S. & R. E. Offeman. Journal of the American Chemical Society 80.6 (1958)]. GO was then mixed with de-ionized water and sonicated until it became clear. The clear solution was treated with hydrazine hydrate and heated to 100° C. in an oil bath for 24 hours. This resulted in the formation of a black precipitate. This precipitate was filtered and washed several times with de-ionized water. The precipitate was finally dried in nitrogen atmosphere for about 6 hours to get pure graphene.

Graphene as obtained above (5 mg/100 mL) was sonicated (Model: Branson 2510) in de-ionized water for an hour at room temperature to yield a homogeneous suspension. To this suspension, chitosan (5 mg) was added and vortexed for one hour at room temperature to yield a chitosan-modified graphene (CMG) suspension. Following this, 5 µL of CMG suspension was pipetted onto the surface of a glassy carbon electrode to serve as the electrochemical platform for the electroanalysis.

Example 2

Characterization of Graphene

The surface of graphene nanosheets was characterized by Raman spectroscopy, Transmission electron microscopy and FT-IR.

Figure 1A:
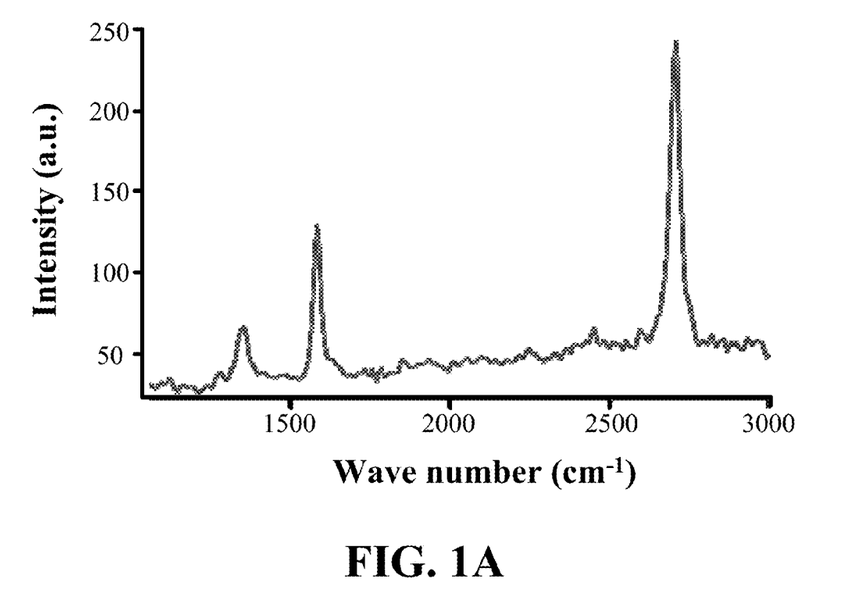

Raman Spectroscopy: Raman measurements were conducted at room temperature with the help of a Reinshaw spectrometer in the back scattering configuration that operates with a 514 nm Ar$^+$ laser at 50 mW. Raman spectra were collected for each sample after a 15 minute exposure time using a high throughput holorographic imaging spectrograph that contains volume transmission grating, holorographic notch filter and a −70° C. Peltier cooled CCD with 4 cm$^{-1}$ resolution. The Raman spectrum of graphene at 514 nm shows a G peak at approximately 1590 cm$^{-1}$ and a 2D peak at approximately 2700 cm$^{-1}$ (FIG. 1A). The G peak is attributed to the doubly degenerate zone center ($E_{2g}$ mode) [Tuinstra, F. & J. L. Koenig. Journal of Chemical Physics 53 (1970); Ferrari, A. C. et al. Physical review letters 97.18 (2006)] and the 2D peak is due to the presence of a pair of phonons with opposite momentum in the highest optical branch near the K [Ferrari, A. C. & J. Robertson. Physical review B 61.20 (2000); Piscanec, S. et al. Physical review letters 93.18 (2004)].

Figure 1B:
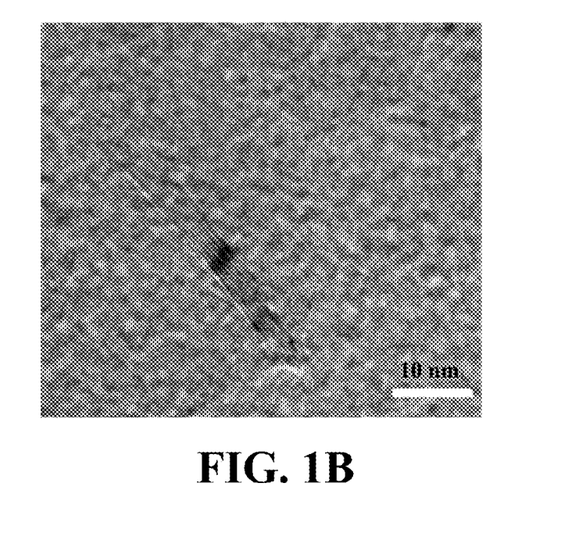

Transmission Electron Microscopy (TEM): TEM measurements were made using TECHNAI F20. The electron source is a Schotty Field emitter operating at 0.7 eV. TECHNAI F20 employed in this work has a point resolution of 0.24 nm, line resolution of 0.102 nm and information limit of 0.14 nm. The number of layers of graphene as determined by the high resolution electron micrograph was found to be 7 and the d value (inter-layer spacing) was calculated to be 0.35 nm (FIG. 1B).

Fourier-Transferred Infra-red Spectroscopy: FTIR characterization of graphene and chitosan modified graphene nanosheets were performed using a Nicolet IR-100 spectrometer. 10 µl (of the sample was dropped onto a disposable polyethylene IR card and the solution was dried under vacuum prior to taking the measurements. The FT-IR spectrum of graphene (FIG. 2) exhibited the IR peaks at 2920 cm$^{-1}$ and 2849 cm$^{-1}$ (sp$^2$ $v_{C-H}$ stretching), 1731 cm$^{-1}$ and 1626 cm$^{-1}$ ($v_{C=O}$), 1481 cm$^{-1}$ (skeletal vibrations of graphene sheets), 1461 cm$^{-1}$ (carboxyl $v_{C-O}$ stretching), 1177 cm$^{-1}$ (alkoxy $v_{C-O}$ stretching at the edges of graphene) and 1051 cm$^{-1}$ ($v_{C-O}$ stretching).

Figure 2:
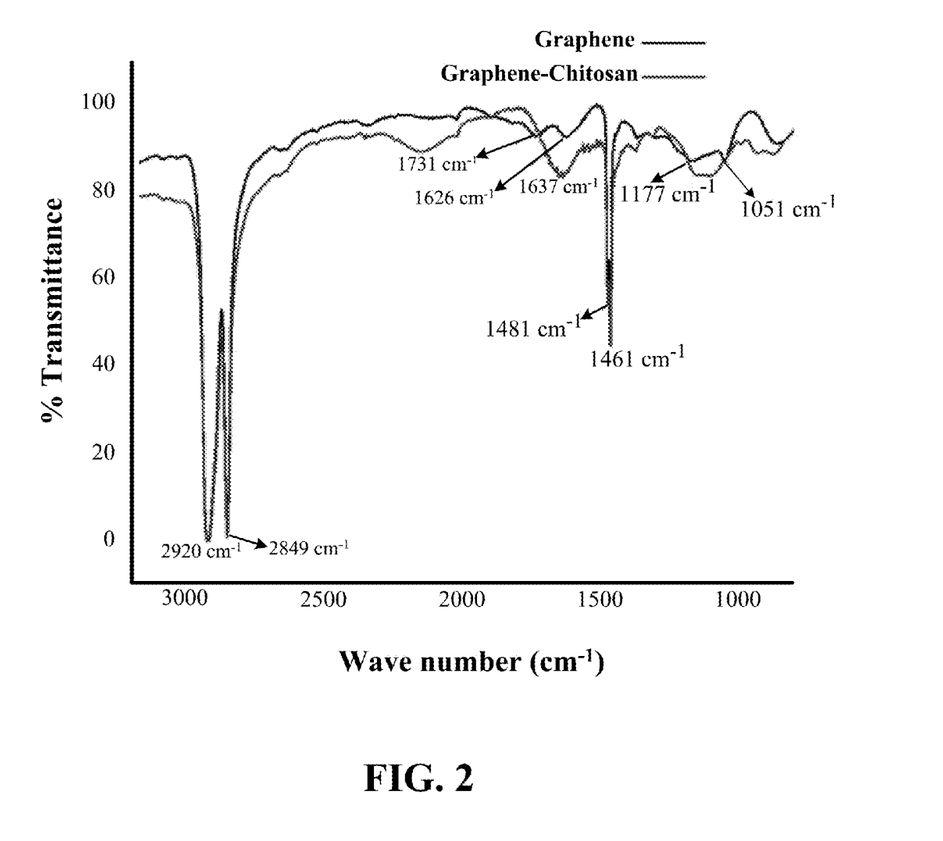
FIG. 2 shows FT-IR spectra of graphene and chitosan-modified graphene.

Then, the graphene surface was covalently modified with chitosan to make the surface more positive and electrostatically trap the capture ssDNA onto the CMG platform. Chitosan modified graphene exhibited all the FT-IR bands as discussed above with the addition of a band at 1635 cm$^{-1}$ ($v_{CONH}$) indicating the covalent modification of graphene with chitosan (FIG. 2).

Example 3

Electrochemical Detection of DNA Mutation

Capture DNA immobilization procedure: 30 pg of capture DNA in 0.1 M Phosphate Buffered Saline (PBS) was pipetted onto the CMG electrode and allowed to remain at room temperature for 15 minutes. The positive charge on the CMG will exert an electrostatic interaction onto the negatively charged phosphate backbone to hold the capture DNA in place. The electrodes were rinsed twice with PBS to remove excess DNA. The amount of capture DNA (30 pg) that needs to be immobilized to achieve a steady and observable signal was optimized by testing a range of DNA concentrations.

Hybridization of Target DNA with capture DNA: The hybridization was performed by pipetting an aliquot of the target DNA in 5×SSC (pH=6.1) onto the electrode coated with the capture DNA and allowing it to remain at room temperature for 30 minutes. The electrodes were then rinsed twice with SSC to remove nonspecifically bound target DNA.

Cyclic voltammetry: The electrochemical readings were performed using a CHI-630A electrochemical analyzer (CH Instruments, Inc.). The working, reference and counter electrode(s) were CMG, Ag/AgCl (3.0M KCl) and platinum wire, respectively. In all experiments, the surface areas of the CMG-modified glassy carbon electrodes, Ag/AgCl and Pt-counter electrodes were identical. All the voltammetric experiments were performed in a 5 mL vial containing the redox probe 0.1 mM $K_4[Fe(CN)_6]^{3-/4-}$ in 1.0 M KCl. Before performing voltammetry, the vial containing the redox probe was purged 2 minutes with nitrogen to remove oxygen.

Figure 3:
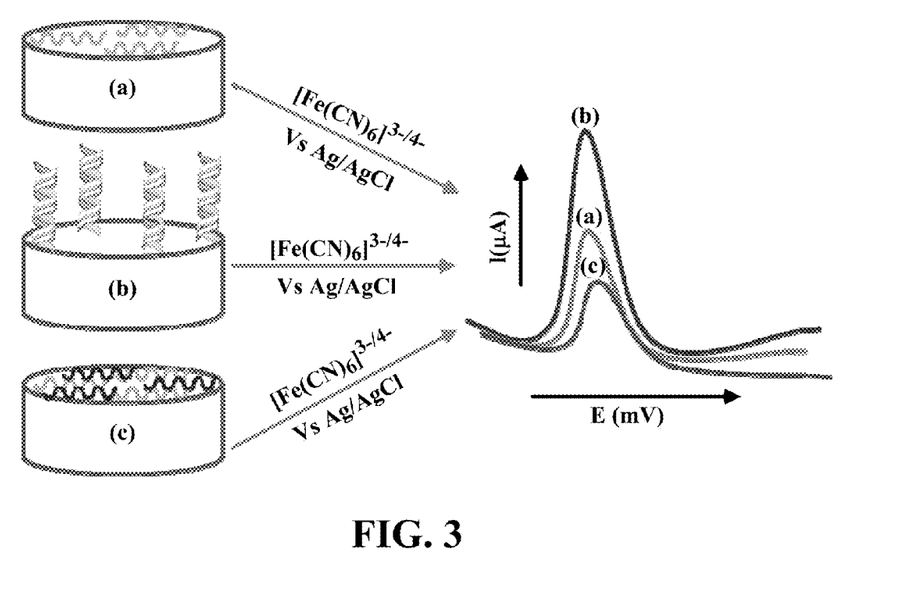
FIG. 3 is an illustration depicting the DNA orientation on a CMG electrode and the corresponding voltammetric response: (a) ssDNA, (b) ssDNA plus complementary DNA, and (c) ssDNA plus mismatch DNA.

In order to determine whether the graphene electrode could identify a mutant DNA, electrodes were loaded with capture DNA then cyclic voltammetry was performed in 0.1 mM $K_4[Fe(CN)_6]^{3-/4-}$/1.0 M KCl with capture ssDNA alone, ssDNA plus complementary DNA and ssDNA plus non-complementary DNA. The introduction of ssDNA onto the CMG surface is expected to sterically hinder the diffusion of the $[Fe(CN)_6]^{3-/4-}$ ions towards the electrode surface. The steric hindrance experienced by the $[Fe(CN)_6]^{3-/4-}$ ions is mainly due to the way in which the ssDNA orients itself on the electrode surface (denoted (a) in FIG. 3). Furthermore, the negatively charged $[Fe(CN)_6]^{3-/4-}$ ions are expected to experience an electrostatic repulsion from the negatively charged phosphate groups on the capture ssDNA. As a result of this combined hindrance, the diffusion of the $[Fe(CN)_6]^{3-/4-}$ towards the electrode surface was restricted compared to an electrode with no DNA (data not shown). Next, the complementary target DNA was applied to the ssDNA-loaded CMG platform. The complementary DNA hybridized perfectly with the capture DNA and a double-stranded structure was formed by hydrogen bonding between the bases. Upon forming the double-stranded helix, the dsDNA is expected to orient itself perpendicular to the electrode platform as shown in scheme (denoted (b) in FIG. 3). This perpendicular orientation causes less steric hindrance to the negatively charged $[Fe(CN)_6]^{3-/4-}$ ions diffusing towards the electrode surface. Also, the formation of hydrogen bonds will weaken the negative charge on the phosphate backbone thereby minimizing the electrostatic repulsion between the dsDNA and the $[Fe(CN)_6]^{3-/4-}$ ions. This explanation was confirmed from the voltammogram obtained in this work using dsDNA modified CMG electrode which showed an increase in the magnitude of the voltammetric peak current (denoted (a) and (b) in FIG. 4).

Figure 4:
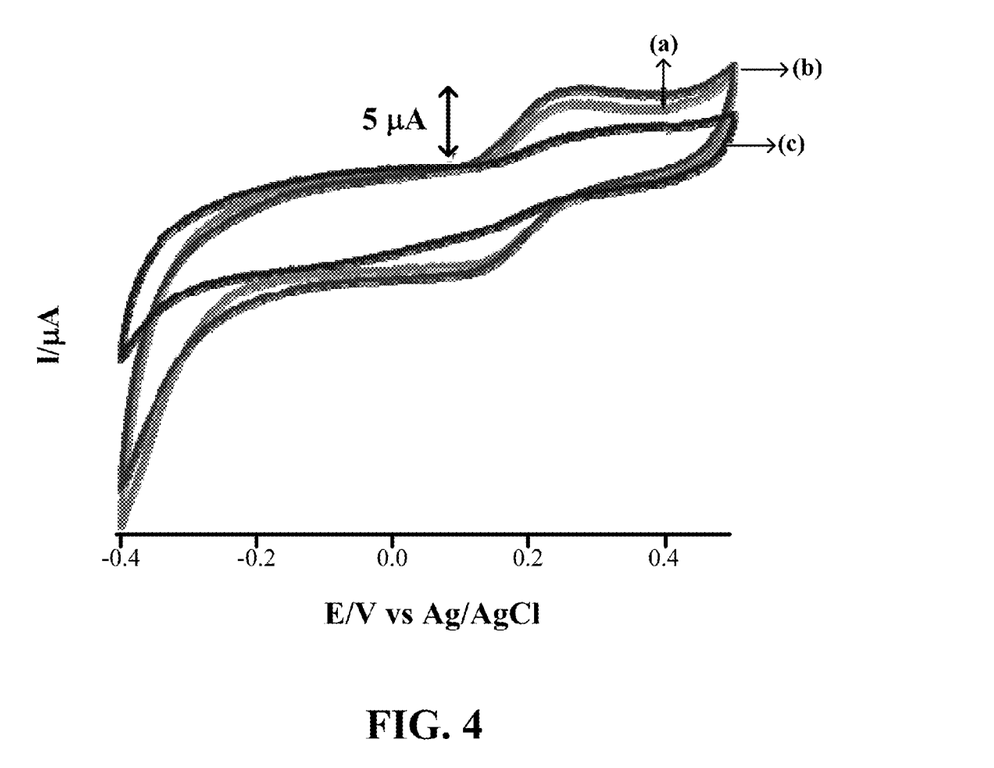
FIG. 4 shows the results of a cyclic voltammogram of the CMG electrode with (a) ssDNA alone, (b) ssDNA plus complementary DNA, and (c) ssDNA plus mismatch DNA.

In the next set of experiments, a non-complementary target DNA was applied onto the ssDNA-modified CMG platform and cyclic voltammetry was performed in 0.1 mM $K_4[Fe(CN)_6]^{3-/4-}$/1.0 M KCl (denoted (c) in FIG. 4). The significant decrease in the magnitude of the peak current seen here is attributed to the major steric and repulsive effect offered to the $[Fe(CN)_6]^{3-/4-}$ ions jointly by the capture and target DNAs. The non-complementary target DNA does not hybridize to the capture ssDNA but it is expected to bind electrostatically to the surface of the CMG electrode itself and cause a severe blockage to the $[Fe(CN)_6]^{3-/4-}$ ions diffusing towards the electrode surface (denoted (c) in FIG. 3). However, there was no significant change in the ΔEp value upon comparison of the electrode with capture DNA versus capture DNA+complementary DNA. Taken together, these experiments, demonstrate that the magnitude of the voltammetric peak current varies in the following order with a negligible variation in their ΔEp value:

$$i_{(complementary\ DNA)} > i_{(capture\ DNA\ alone)} > i_{(noncomplementary\ DNA)}.$$

The invention claimed is:

1. A device for detecting non-hybridization of a single stranded target polynucleotide sequence and a single stranded capture polynucleotide sequence as compared to a control, comprising a glassy carbon electrode (GCE) coated with a chitosan-graphene nanosheet material, wherein the chitosan-graphene nanosheet material is prepared using an approximately 0.005% (w/v) graphene and 0.005% (w/v) chitosan solution, and wherein the capture polynucleotide is attached to the chitosan-graphene nanosheet material.

2. The device of claim 1, wherein an FT-IR spectrum analysis of the chitosan-graphene nanosheet material exhibits IR peaks at approximately 2920 $cm^{-1}$ and 2849 $cm^{-1}$ ($sp^2$ $v_{C-H}$ stretching), approximately 1731 $cm^{-1}$ and 1626 $cm^{-1}$ ($v_{C=O}$), approximately 1481 $cm^{-1}$ (skeletal vibrations of graphene sheets), approximately 1461 $cm^{-1}$ (carboxyl $v_{C-O}$ stretching), approximately 1177 $cm^{-1}$ (alkoxy $v_{C-O}$ stretching at the edges of graphene), approximately 1051 $cm^{-1}$ ($v_{C-O}$ stretching), and approximately 1635 $cm^{-1}$ ($v_{CONH}$).

3. A method for making a device for detecting non-hybridization of a single stranded target polynucleotide sequence and a single stranded capture polynucleotide sequence as compared to a control, comprising providing a glassy carbon electrode (GCE) and coating the GCE with a chitosan-graphene nanosheet material, wherein the chitosan-graphene nanosheet material is prepared using an approximately 0.005% (w/v) graphene and 0.005% (w/v) chitosan solution, and wherein the capture polynucleotide is attached to the chitosan-graphene nanosheet material.

4. The method of claim 3, wherein an FT-IR spectrum analysis of the chitosan-graphene nanosheet material exhibits IR peaks at approximately 2920 $cm^{-1}$ and 2849 $cm^{-1}$ ($sp^2$ $v_{C-H}$ stretching), approximately 1731 $cm^{-1}$ and 1626 $cm^{-1}$ ($v_{C=O}$), approximately 1481 $cm^{-1}$ (skeletal vibrations of graphene sheets), approximately 1461 $cm^{-1}$ (carboxyl $v_{C-O}$ stretching), approximately 1177 $cm^{-1}$ (alkoxy $v_{C-O}$ stretching at the edges of graphene), approximately 1051 $cm^{-1}$ ($v_{C-O}$ stretching), and approximately 1635 $cm^{-1}$ ($v_{CONH}$).

5. A method for detecting non-hybridization of a single stranded target polynucleotide sequence and a single stranded capture polynucleotide sequence, comprising:
   a. providing a glassy carbon electrode (GCE) coated with a chitosan-graphene nanosheet material having the capture polynucleotide attached thereto, wherein the chitosan-graphene nanosheet material is prepared using an approximately 0.005% (w/v) graphene solution;
   b. adding the target polynucleotide to the GCE and allowing sufficient time for binding of the capture and target polynucleotides;
   c. removing the unbound target polynucleotide; and
   subjecting the GCE to cyclic voltammetry, wherein a decrease in a voltammetric peak as compared to a hybridizing control polynucleotide indicates non-hybridization of the capture and target polynucleotides.

6. A method for detecting non-hybridization of a single stranded target polynucleotide sequence and a single stranded capture polynucleotide sequence, comprising:
   a. providing a glassy carbon electrode (GCE) coated with a chitosan-graphene nanosheet material having the capture polynucleotide attached thereto, wherein the chitosan-graphene nanosheet material is prepared using an approximately 0.005% (w/v) chitosan solution;
   b. adding the target polynucleotide to the GCE and allowing sufficient time for binding of the capture and target polynucleotides;
   c. removing the unbound target polynucleotide; and
   d. subjecting the GCE to cyclic voltammetry, wherein a decrease in a voltammetric peak as compared to a hybridizing control polynucleotide indicates non-hybridization of the capture and target polynucleotides.

7. A method for detecting non-hybridization of a single stranded target polynucleotide sequence and a single stranded capture polynucleotide sequence, comprising:
   a. providing a glassy carbon electrode (GCE) coated with a chitosan-graphene nanosheet material having the capture polynucleotide attached thereto, wherein chitosan-graphene ratio is approximately 1:1;
   b. adding the target polynucleotide to the GCE and allowing sufficient time for binding of the capture and target polynucleotides;
   c. removing the unbound target polynucleotide; and
   d. subjecting the GCE to cyclic voltammetry; wherein a decrease in a voltammetric peak as compared to a hybridizing control polynucleotide indicates non-hybridization of the capture and target polynucleotides.

8. A method for detecting a mutation in a single stranded target polynucleotide sequence and a single stranded capture polynucleotide sequence, comprising:
   a. providing a glassy carbon electrode (GCE) coated with a chitosan-graphene nanosheet material having the capture polynucleotide attached thereto, wherein the chitosan-graphene nanosheet material is prepared using an approximately 0.005% (w/v) graphene solution;

b. adding the target polynucleotide to the GCE and allowing sufficient time for binding of the capture and target polynucleotides;

c. removing the unbound target polynucleotide; and subjecting the GCE to cyclic voltammetry, wherein a decrease in a voltammetric peak as compared to a hybridizing control polynucleotide indicates a mutation of the capture in the target polynucleotide as compared to the control.

9. A method for detecting a mutation in a single stranded target polynucleotide sequence and a single stranded capture polynucleotide sequence, comprising:

a. providing a glassy carbon electrode (GCE) coated with a chitosan-graphene nanosheet material having the capture polynucleotide attached thereto, wherein the chitosan-graphene nanosheet material is prepared using an approximately 0.005% (w/v) chitosan solution;

b. adding the target polynucleotide to the GCE and allowing sufficient time for binding of the capture and target polynucleotides;

c. removing the unbound target polynucleotide; and d. subjecting the GCE to cyclic voltammetry, wherein a decrease in a voltammetric peak as compared to a hybridizing control polynucleotide indicates a mutation of the capture in the target polynucleotide as compared to the control.

10. A method for detecting a mutation in a single stranded target polynucleotide sequence and a single stranded capture polynucleotide sequence, comprising:

a. providing a glassy carbon electrode (GCE) coated with a chitosan-graphene nanosheet material having the capture polynucleotide attached thereto, wherein chitosan-graphene ratio is approximately 1:1;

b. adding the target polynucleotide to the GCE and allowing sufficient time for binding of the capture and target polynucleotides;

c. removing the unbound target polynucleotide; and d. subjecting the GCE to cyclic voltammetry, wherein a decrease in a voltammetric peak as compared to a hybridizing control polynucleotide indicates a mutation of the capture in the target polynucleotide as compared to the control.

\* \* \* \* \*